United States Patent
Smith et al.

(10) Patent No.: US 11,413,027 B2
(45) Date of Patent: Aug. 16, 2022

(54) TISSUE RETRACTION DEVICE

(71) Applicant: Boston Scientific Scimed, Inc., Maple Grove, MN (US)

(72) Inventors: Paul Smith, Smithfield, RI (US); Scott Brechbiel, Acton, MA (US); Ryan Wales, Northborough, MA (US); Danny Lee, Framingham, MA (US); Samuel Raybin, Marlborough, MA (US); Niklas Andersson, Wayland, MA (US); Jialiang Wang, Smithfield, RI (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 233 days.

(21) Appl. No.: 16/668,011

(22) Filed: Oct. 30, 2019

(65) Prior Publication Data
US 2020/0060673 A1 Feb. 27, 2020

Related U.S. Application Data

(63) Continuation of application No. 15/720,208, filed on Sep. 29, 2017, now Pat. No. 10,537,316.
(Continued)

(51) Int. Cl.
*A61B 17/02* (2006.01)
*A61B 1/32* (2006.01)
*A61B 17/00* (2006.01)

(52) U.S. Cl.
CPC .......... *A61B 17/0218* (2013.01); *A61B 1/32* (2013.01); *A61B 17/0206* (2013.01);
(Continued)

(58) Field of Classification Search
CPC .... A61B 2017/0212; A61B 2017/0225; A61B 17/0218
See application file for complete search history.

(56) References Cited

U.S. PATENT DOCUMENTS 5,337,736 A * 8/1994 Reddy ................ A61B 17/0218
128/898
7,156,862 B2 * 1/2007 Jacobs ................ A61B 17/064
606/215

(Continued)

FOREIGN PATENT DOCUMENTS

CN 201267462 Y 7/2009
CN 102811671 A 12/2012
(Continued)

OTHER PUBLICATIONS

ProdiGI™ traction wire.—Medtronic—2020.

*Primary Examiner* — Christian A Sevilla
(74) *Attorney, Agent, or Firm* — Seager, Tufte & Wickhem, LLP

(57) ABSTRACT

The present disclosure relates to the field of tissue dissection. Specifically, the present disclosure relates to medical devices which lift and retract tissue during a dissection procedure to improve visualization of the target tissue and mitigate obstruction of dissection tools. In particular, the present disclosure relates to a tissue retraction device which moves from a constrained to relaxed configuration to immobilize and retract the dissected portion of target tissue during a dissection procedure.

20 Claims, 15 Drawing Sheets

Related U.S. Application Data

(60) Provisional application No. 62/402,649, filed on Sep. 30, 2016.

(52) U.S. Cl.
CPC . *A61B 17/0281* (2013.01); *A61B 2017/00269* (2013.01); *A61B 2017/00314* (2013.01); *A61B 2017/00331* (2013.01); *A61B 2017/00818* (2013.01); *A61B 2017/00862* (2013.01); *A61B 2017/00867* (2013.01); *A61B 2017/0212* (2013.01); *A61B 2017/0225* (2013.01); *A61B 2017/0287* (2013.01)

(56) References Cited

U.S. PATENT DOCUMENTS

| | | | |
|---|---|---|---|
| 10,206,669 B2 | 2/2019 | Bhatt et al. | |
| 2010/0174150 A1* | 7/2010 | Park | A61B 17/0218 600/218 |
| 2011/0282365 A1* | 11/2011 | Hadba | A61L 31/14 606/151 |
| 2016/0113717 A1* | 4/2016 | Csernatoni | A61B 17/0218 128/850 |

FOREIGN PATENT DOCUMENTS

| | | |
|---|---|---|
| EP | 0584526 A1 | 3/1994 |
| JP | 2012506300 A | 3/2012 |
| JP | 2015516853 A | 6/2015 |
| WO | 03061751 A1 | 7/2003 |

\* cited by examiner

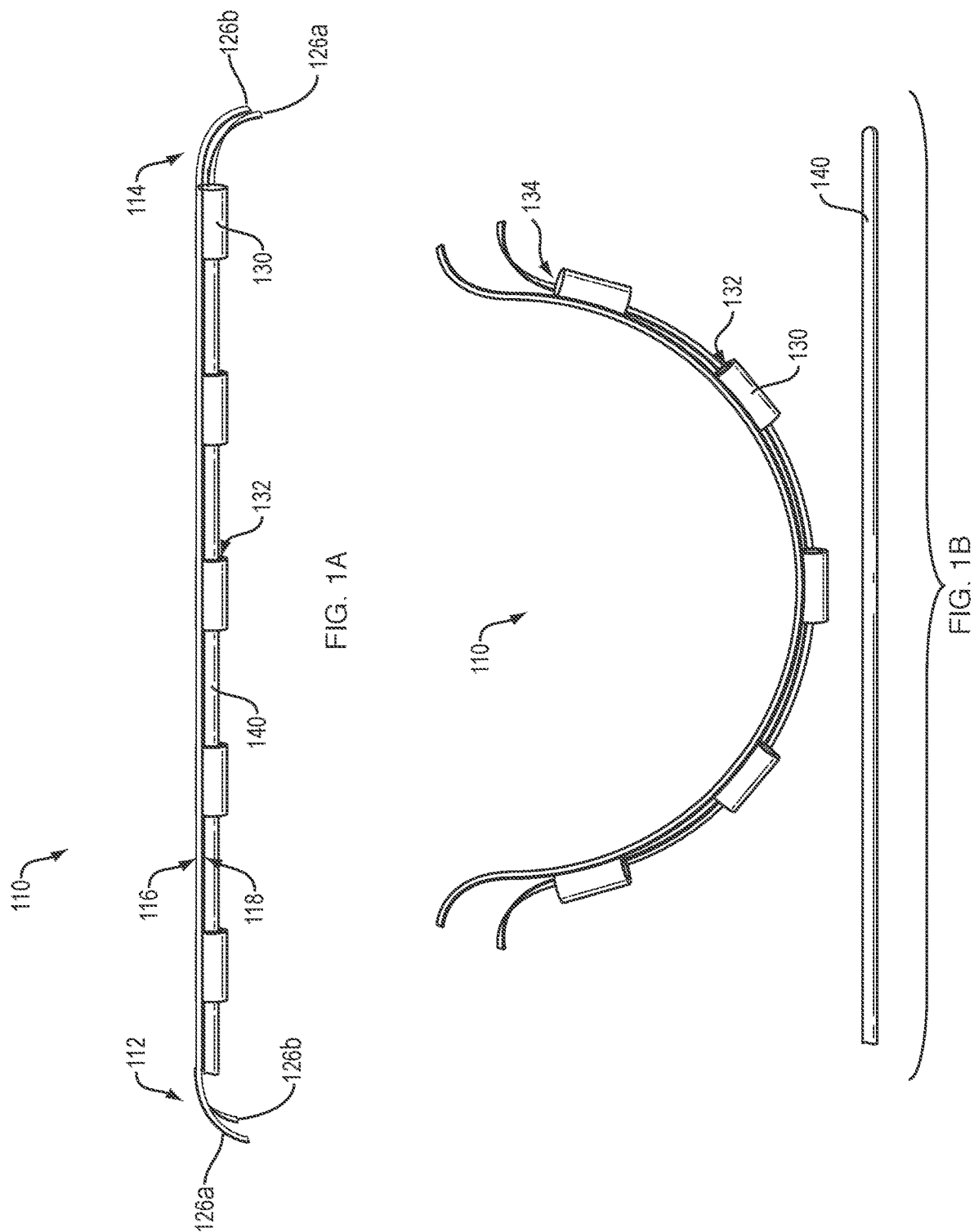

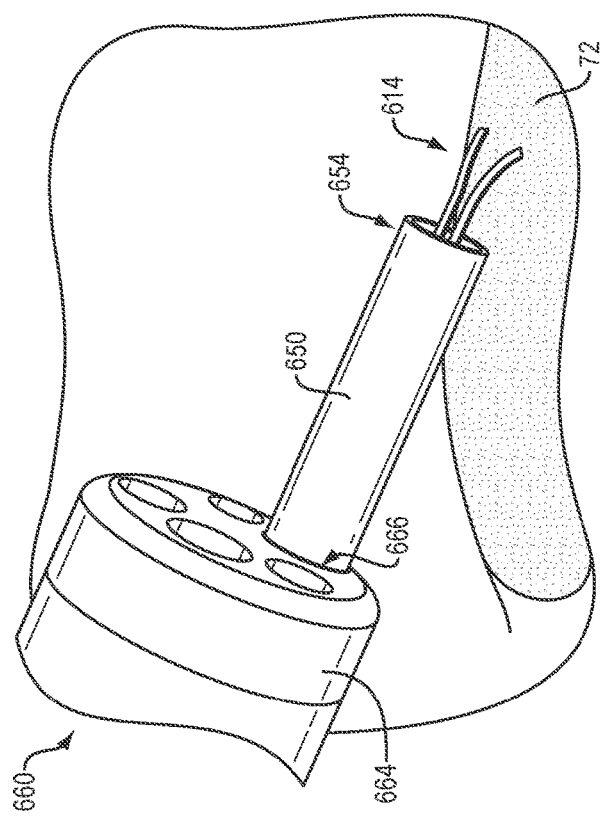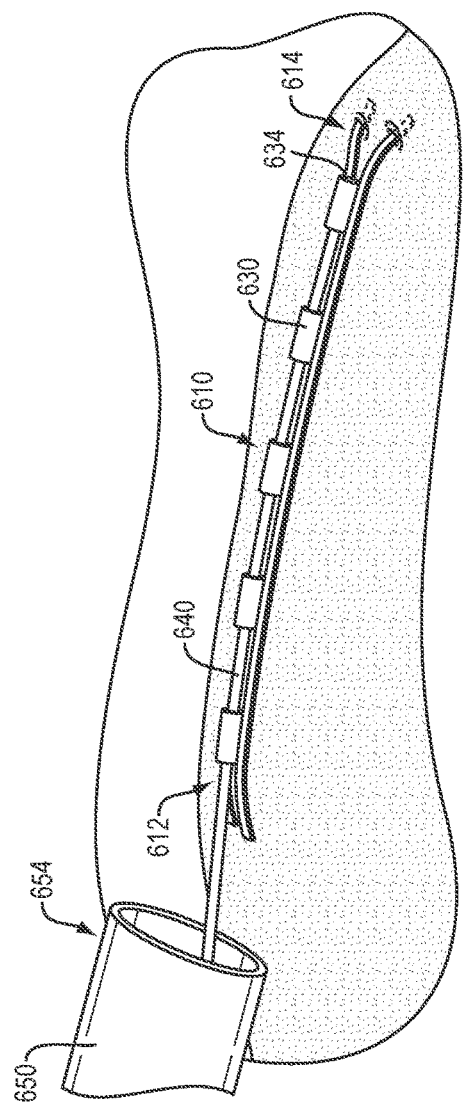

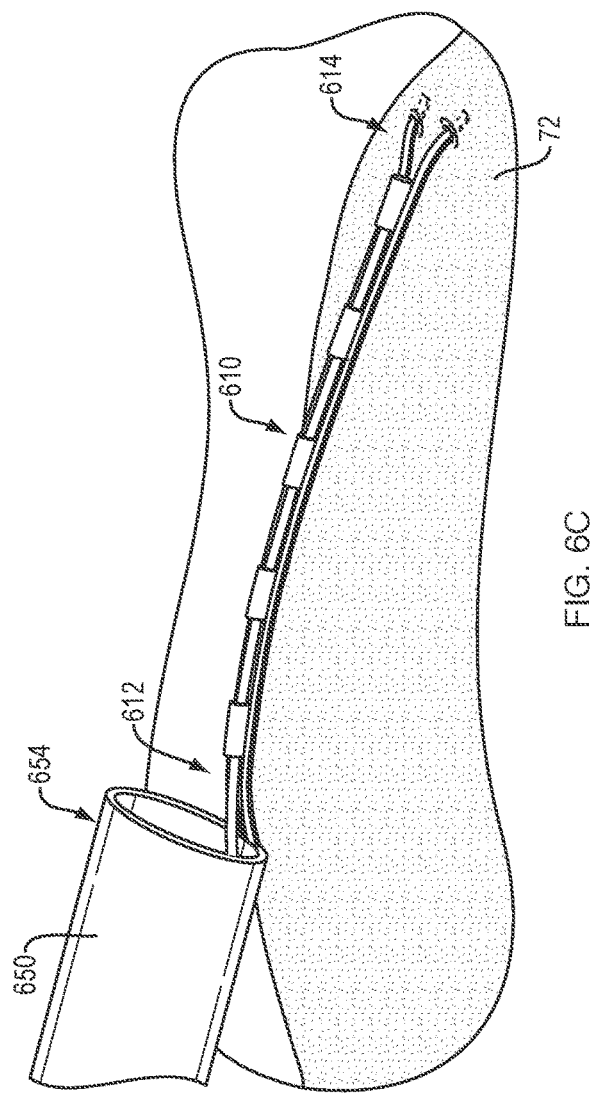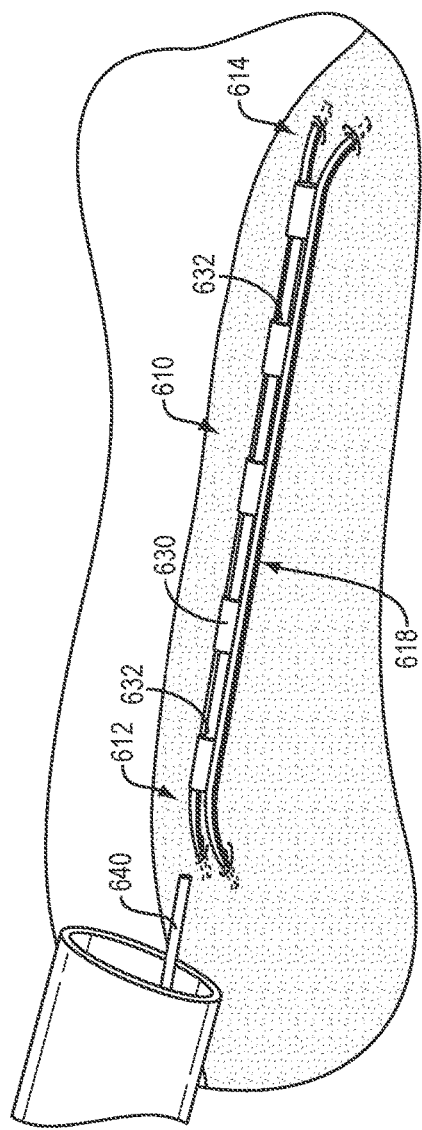
FIG. 6C
FIG. 6D

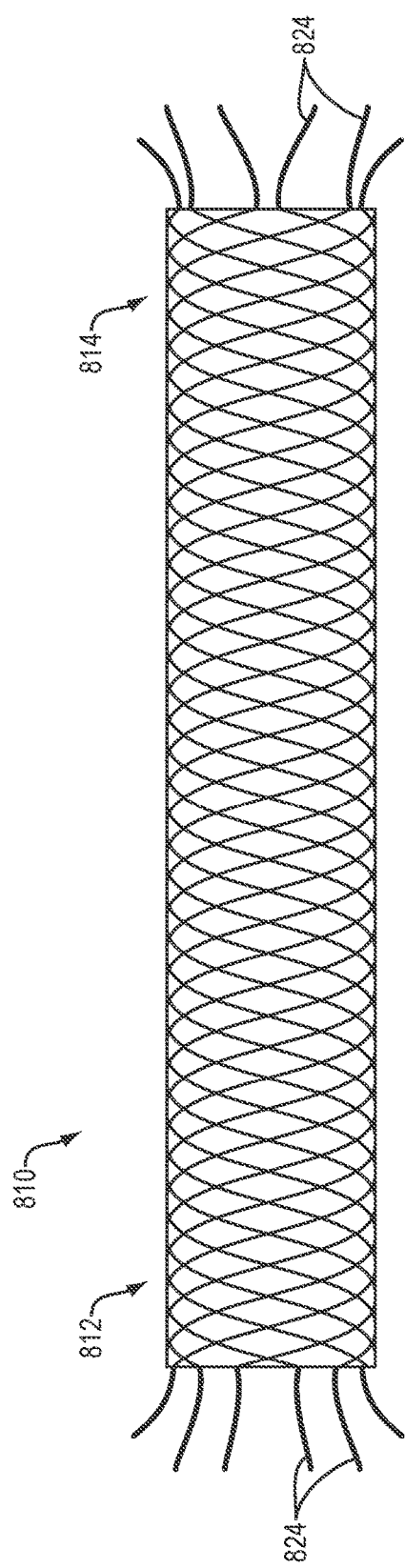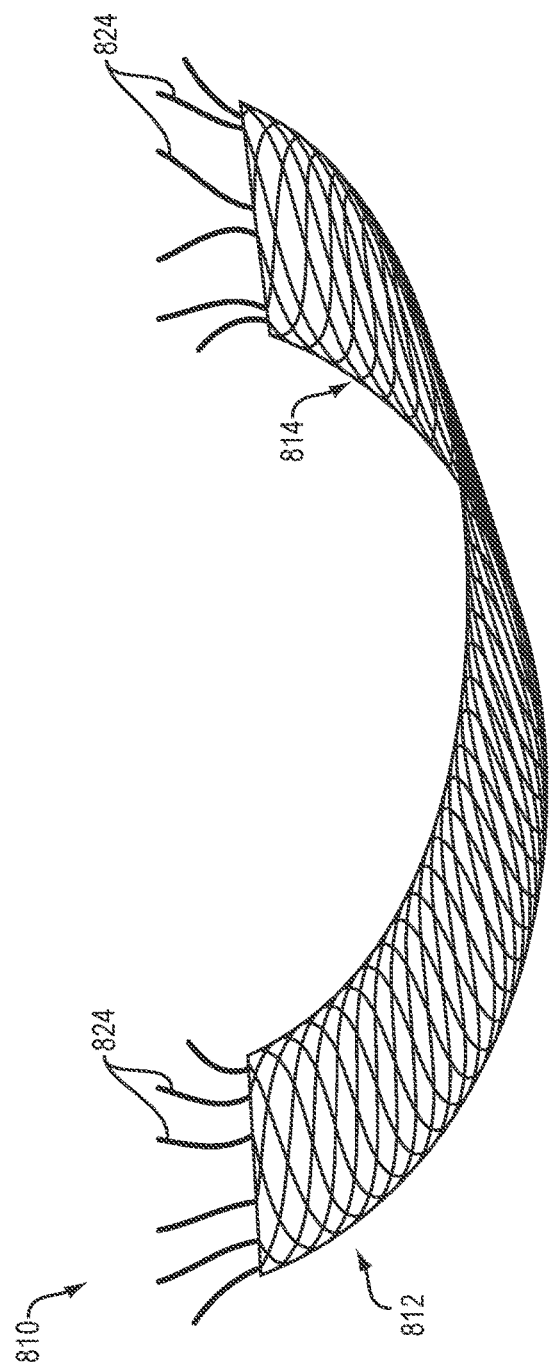

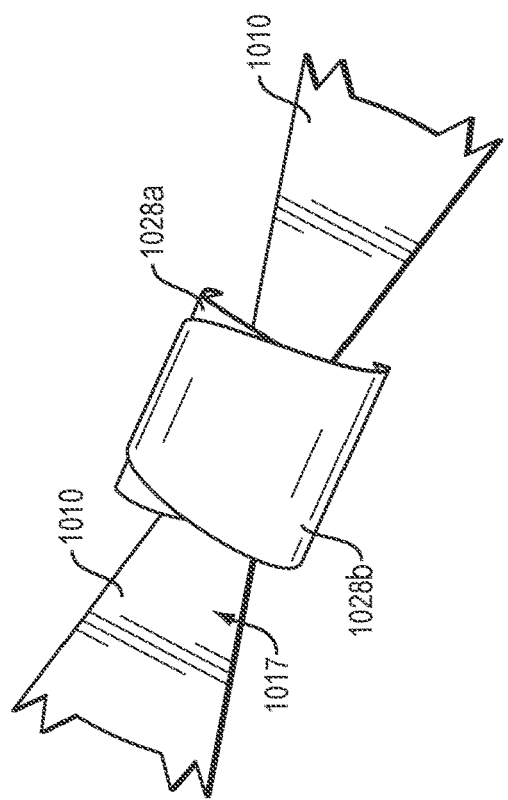
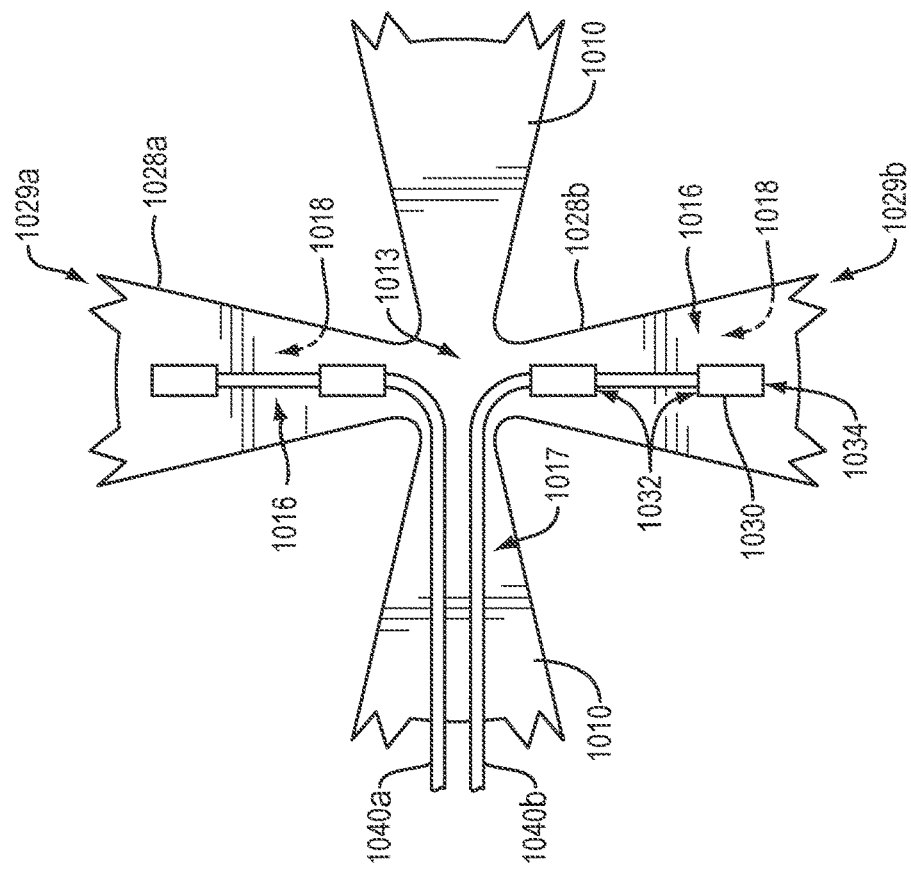

TISSUE RETRACTION DEVICE

CROSS REFERENCE TO RELATED APPLICATIONS

This application is a continuation of Ser. No. 15/720,208, filed on Sep. 29, 2017 and titled "Tissue Retraction Device," which claims the benefit of priority under 35 USC § 119 to U.S. Provisional Patent Application Ser. No. 62/402,649, filed on Sep. 30, 2016 and titled "Tissue Retraction Device," which is incorporated herein by reference in its entirety for all purposes.

FIELD

The present disclosure relates to the field of tissue dissection. Specifically, the present disclosure relates to medical devices which lift and retract tissue during a dissection procedure to improve visualization of the target tissue and mitigate obstruction of dissection tools. In particular, the present disclosure relates to a tissue retraction device which moves from a constrained to relaxed configuration to immobilize and retract the dissected portion of target tissue during a dissection procedure.

BACKGROUND

Surgical dissection of lesions from within narrow body passages, such as the digestive tract, may be inefficient and time-consuming due to poor target tissue visualization during the dissection procedure. This problem may be exacerbated during the procedure, as the partially dissected target tissue obstructs the working area to further decrease visibility and obstruct the dissection tools.

SUMMARY

The present disclosure, in its various aspects, relates to a tissue retraction device which immobilizes and retracts a target tissue during a dissection procedure for improved tissue visualization and manipulation.

In one aspect, the present disclosure relates to a tissue retractor, comprising an elongate flexible element, which includes a proximal end configured to engage a first target tissue portion, and a distal end configured to engage a second target tissue portion; and at least one guide member attached to the elongate flexible element, wherein the at least one guide member defines a lumen extending therethrough. The elongate flexible element moves between a first (i.e., constrained, confined, stored or delivery) and a second (i.e., relaxed, free or deployed configuration) configuration.

In another aspect, the present disclosure relates to a tissue retractor, comprising an elongate flexible element, which includes a proximal end configured to engage a first target tissue portion, and a distal end configured to engage a second target tissue portion; at least one guide member attached to the elongate flexible element, wherein the at least one guide member defines a lumen extending therethrough; and a control wire configured to be slidably received within the lumen of the at least one guide member, wherein the elongate flexible element moves between a first (i.e., constrained, confined, stored or delivery) configuration when the control wire is disposed within the lumen of the at least one guide member, and a second (i.e., relaxed, free or deployed configuration) configuration when the control wire is not disposed within the lumen of the at least one guide member. The at least one guide member may include a plurality of guide members attached along a length of the elongate flexible element. An end of the at least one guide member may include a cap. The elongate flexible element may be substantially planar when in the first configuration. The elongate flexible element may curve along its longitudinal axis when in the second configuration. The elongate flexible element may include a woven-mesh. In addition, or alternatively, the elongate flexible element comprises two or more parallel elements. The two or more parallel elements may be attached to each other by the at least one guide member. A portion of the parallel elements may be configured to bow outward from a longitudinal axis of the elongate flexible element. The control wire may pass between the parallel elements when disposed within the lumen of the at least one guide member. The proximal and distal ends of the elongate flexible element may include one or more tissue anchors, e.g., tines, forks, hooks, fingers, barbs, loops and/or clips. In addition, or alternatively, one or more stabilizers, e.g., hooks and/or barbs, etc., may be attached to the elongate flexible element. The elongate flexible element may be formed from a polymer including, but not limited to, acrylate-based polymers, polyurethane-based polymers, polynorbornene-based polymers and polylactide-based polymers. In addition, or alternatively, the elongate flexible element may be formed from a metal or metal alloy including, but not limited to, platinum, tungsten, titanium, stainless steel, nickel, nickel-titanium alloys and other alloys of the above or other metals.

In yet another aspect, the present disclosure relates to a system, comprising a delivery catheter, and an elongate flexible element slidably disposed within a lumen of the delivery catheter. The elongate flexible element may include a proximal end configured to engage a first target tissue portion; a distal end configured to engage a second target tissue portion; at least one guide member attached to the elongate flexible element, wherein the at least one guide member may define a lumen extending therethrough; and a control wire configured to be slidably received within the lumen of the at least one guide member. The elongate flexible element may move between a first (i.e., constrained, confined, stored or delivery) configuration when the control wire is disposed within the lumen of the at least one guide member, and a second (i.e., relaxed, free or deployed configuration) configuration when the control wire is not disposed within the lumen of the at least one guide member. A proximal end of the control wire may extend beyond a proximal end of the delivery catheter. The delivery catheter may be slidably disposed within a working channel of an endoscope. In addition, or alternatively, the at least one guide member may be attached along a length of the elongate flexible element.

In yet another aspect, the present disclosure relates to a method, comprising advancing a delivery catheter through a working channel of an endoscope to a position adjacent to a target tissue such that a distal end of the delivery catheter is above a first portion of the target tissue, wherein a working channel of the delivery catheter includes an elongate flexible element comprising a proximal end configured to engage a first target tissue portion, a distal end configured to engage a second target tissue portion, at least one guide member attached to the elongate flexible element, wherein the at least one guide member defines a lumen extending therethrough, and a control wire configured to be slidably received within the lumen of the at least one guide member, wherein the elongate flexible element moves between a first configuration when the control wire is disposed within the lumen of the at least one guide member, and a second configuration when the control wire is not disposed within the lumen of the at least one guide member; distally advancing the control wire such that the distal end of the elongate flexible element engages the first portion of the target tissue beyond the distal end of the delivery catheter; proximally retracting the delivery catheter such that the proximal end of the elongate flexible element moves beyond the distal end of the delivery catheter; urging the distal end of the delivery catheter against the proximal end of the elongate flexible element such that the proximal end of the elongate flexible element engages a second portion of the target tissue; and proximally retracting the control wire such that the control wire is removed from within the lumen of the at least one guide member. The method may further include advancing a tissue removal, e.g., cutting, element through the working channel of the endoscope, and dissecting along the margins of the target tissue as the elongate flexible element moves from the first configuration to the second configuration.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIGS. 1A-1B illustrate a tissue retractor in constrained planar (FIG. 1A) and relaxed curved (FIG. 1B) configurations, according to an embodiment of the present disclosure.

FIGS. 6A-6D illustrate a method to deploy a tissue retractor onto a target tissue, according to an embodiment of the present disclosure.

FIGS. 8A-8B illustrate a tissue retractor in constrained planar (FIG. 8A) and relaxed curved (FIG. 8B) configurations, according to another embodiment of the present disclosure.

FIGS. 10A-10B illustrate a tissue retractor in constrained (FIG. 10A) and relaxed (FIG. 10B) configurations, according to another embodiment of the present disclosure.

Figure 2A:
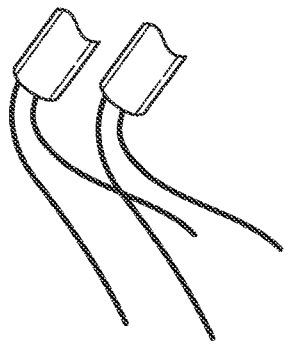
FIGS. 2A-2D illustrate various tissue anchor configurations which may be disposed on end portions of a tissue retractor, according to embodiments of the present disclosure.
Figure 2B:
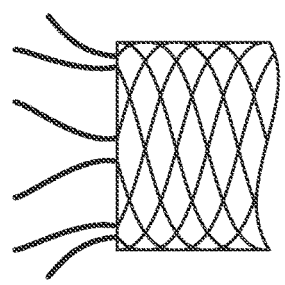
Figure 2C:
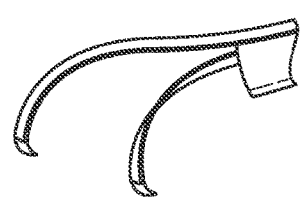
Figure 2D:
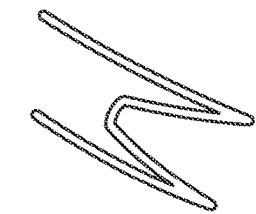

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to medical devices and systems for dissecting tissues of the digestive system, it should be appreciated that such medical devices may be used to dissect tissues of the abdominal cavity, gastrointestinal system, thoracic cavity and the like. Moreover, a variety of medical procedures may benefit from presently disclosed medical devices, including, for example, Endoscopic Submucosal Dissection (ESD), Peroral Endoscopic Myotomy (POEM), cholecystectomy and Video-Assisted Thorascopic Surgery (VATS) procedures.

As used herein, the term "distal" refers to the end farthest away from a medical professional when introducing a device into a patient, while the term "proximal" refers to the end closest to the medical professional when introducing a device into a patient.

As used herein, the term "tissue retraction" or "retraction," refers to the ability to control the position of a tissue during a dissection procedure. For example, "retraction" may allow the dissected portion of a target tissue to be immobilized and lifted away from the cutting plane to improve visualization of the remaining (i.e., non-dissected) target tissue, while also applying tension to the target tissue for more precise manipulation of the cutting element.

As used herein, the term "target tissue" refers to an unhealthy, diseased (i.e., cancerous, pre-cancerous etc.) or otherwise undesirable portion of tissue. A "target tissue" may also include tissues that are suspected of being unhealthy or diseased, but which require surgical removal for verification of their disease status by biopsy. It should be appreciated that surgical dissection of a "target tissue" typically includes removal of a portion of the surrounding healthy tissue along the "target tissue" margin to ensure complete removal and minimize the potential for metastasis of left behind or dislodged "target tissue" cells to other body locations.

In one embodiment, the present disclosure provides a tissue retraction device which improves target tissue visibility and access during a dissection procedure by retracting and immobilizing the dissected target tissue portion, including without occupying and/or obstructing a working channel of the endoscope. As illustrated in FIGS. 1A-1B, in one embodiment, a tissue retractor of the present disclosure may include an elongate flexible element 110 (e.g., spine) comprising a proximal end 112 configured to engage a first target tissue portion, a distal end 114 configured to engage a second target tissue portion, a first surface 116 (i.e., top or upper surface) and a second surface 118 (i.e., bottom or lower surface). A plurality of guide members 130 may be disposed along a length of the elongate flexible element 110. Although the guide members 130 of FIGS. 1A-1B are substantially evenly spaced along the second surface 118 of the elongate flexible element 110, it should be appreciated that the guide members may be disposed on either of the first and/or second surfaces 116, 118 in a uniform or non-uniform pattern. Alternatively, the guide members may be tangential or coplanar with either the first or second surface 116, 118 of the elongate flexible element 110. In addition, although the elongate flexible element 110 illustrated in FIGS. 1A-1B includes five guide members 130, it should be appreciated that the number of guide members 130 may be less than five (i.e., four or fewer) or greater than five (i.e., six or more). Although depicted as circular, the guide members could be any one of a variety of shapes in cross-section, e.g., semi-circular, oval, square, rectangular, etc. The elongate flexible element may include a variety of lengths (e.g., approximately 6.0 inches; approximately 5.0 inches; approximately 4.0 inches; approximately 3.0 inches; approximately 2.75 inches; approximately 2.0 inches; approximately 1.5 inches; approximately 1.0 inches). Each guide member 130 may define a lumen 132 extending therethrough. In one embodiment, an end of the distal-most guide member 130 (i.e., the guide member closest to the distal end 114 of the elongate flexible element 110) may include a cap 134. In one embodiment, the elongate flexible element 110 may comprise parallel elements or wires 126a, 126b connected to each other by the plurality of guide members 130. The tissue retractor may further include control wire 140 (e.g., restraining mandrel) configured to be slidably received by the respective lumens 132 of each guide member 130 along a longitudinal axis of the elongate flexible element 110. Referring to FIG. 1A, when the control wire 140 is disposed within the respective lumens 132 of each guide member 130, the elongate flexible element 110 is maintained in a first configuration (i.e., constrained, confined, stored or delivery configuration). Referring to FIG. 1B, when the control wire 140 is not disposed within (i.e., removed from) the respective lumens 132 of each guide member 130, the elongate flexible element 110 moves to a second configuration (i.e., relaxed, free or deployed configuration).

In the first configuration, the elongate flexible element 110 includes a flat or planar configuration such that substantially all of the second surface 118 is placed in contact with the tissue surface. In one embodiment, the elongate flexible element 110 may include a width and a thickness, wherein the width exceeds the thickness such that the elongate flexible element 110 resists the tendency to roll or twist during a dissection procedure. For example, the elongate flexible element may include a width (e.g., approximately 0.070 inches; approximately 0.065 inches; approximately 0.060 inches; approximately 0.055 inches; approximately 0.050 inches) that is greater than the thickness (e.g., approximately 0.040 inches; approximately 0.035 inches; approximately 0.030 inches; approximately 0.025 inches; approximately 0.020 inches), in some cases the width may be as much as approximately two times greater than the thickness. The elongate flexible element 110 may be made, for example, from a variety of resilient biocompatible materials, including metals and metal alloys such as platinum, tungsten, titanium, stainless steel, nickel and nickel-titanium alloys (e.g., nitinol), polymers such as acrylate-based polymers, polyurethane-based polymers, polynorbornene-based polymers, and polylactide-based polymers, and any combinations thereof.

It should be appreciated that the "force" stored within such materials when in the constrained configuration allows the elongate flexible element 110 to apply and maintain constant upward lifting/retraction pressure against the tissue in which it is embedded. The natural tendency of the elongate flexible element 110 to move (i.e., return) from the flat or planar shape of the first configuration, to the curved (e.g., round or hemispherical) shape of the second configuration allows the dissected portions of the target tissue to be lifted or elevated above the cutting plane such that the non-dissected target tissue portion may be more easily visualized and more efficiently excised. The shape of the second configuration may be controlled during manufacturing the elongate flexible element 110 so as to impart or set a desired memory in the elongate flexible element material that is assumed in the relaxed, unconstrained position.

Referring to FIGS. 2A-2D, the proximal and distal ends 112, 114 of the elongate flexible element 110 may include a variety of anchor configurations, including, by way of non-limiting example, wire prongs or tines (FIG. 2A), wire forks, fingers or hooks (FIG. 2B), wire ends (FIG. 2C) and/or loops, clips or barbs (FIG. 2D) to prevent the elongate flexible element 110 from disengaging from the tissue surface prior to completion of the dissection procedure. In addition, or alternatively, the proximal and distal ends 112, 114 may beneficially include sharpened or pointed tips to facilitate tissue penetration. In one embodiment, these (and other) wire anchor configurations may comprise a shape memory material, e.g., nitinol, which is heat set to point downwards when deployed, but may be constrained in a straight position within a delivery catheter prior to deployment. When embedded within the target tissue, the proximal and distal ends 112, 114 exert upward (e.g., lifting) and outward (e.g., longitudinal) retraction forces into the target tissue, while simultaneously driving or pressing the second surface 118 of the elongate flexible element 110 downward against the target tissue surface.

Figure 3:
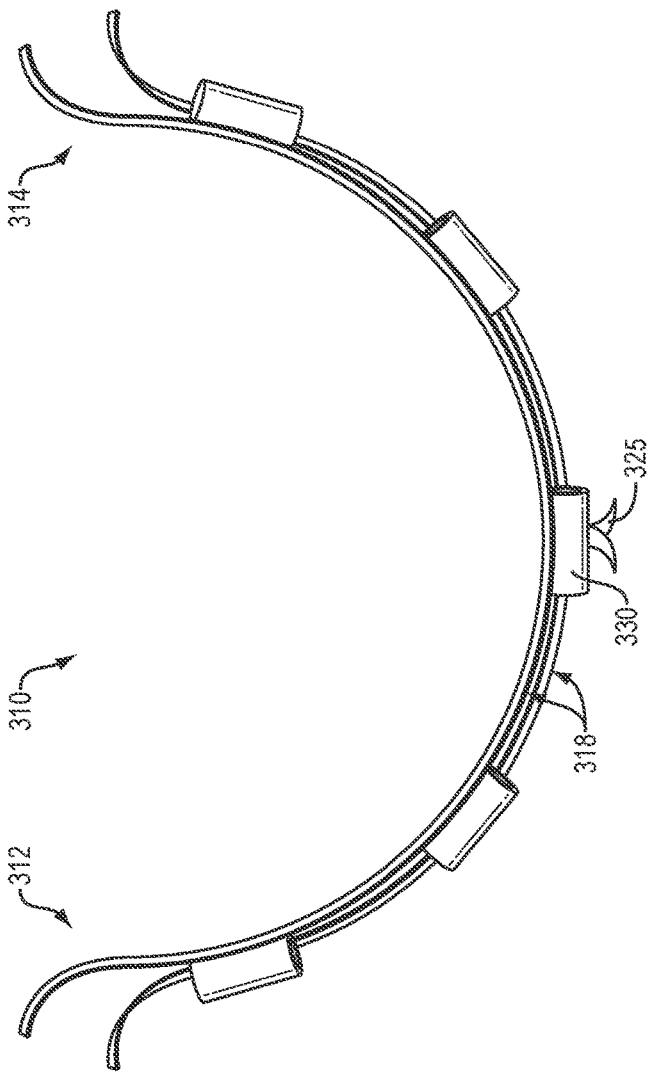
FIG. 3 illustrates a tissue stabilizer disposed on the bottom surface of a tissue retractor, according to an embodiment of the present disclosure.

Referring to FIG. 3, in one embodiment, one or more stabilizers 325 (e.g., hook, barb, etc.) may be disposed along and extend outward from the one or more of the guide members 330 attached to the second surface 318 of the elongate flexible element 310. The pressure applied along the second surface 318 of the elongate flexible element 310 against the target tissue allows such stabilizer(s) 325 to engage additional portions of the target tissue between the proximal and distal ends 312, 314. The additional tissue engagement provided by the stabilizer(s) 325 may further prevent or minimize any tendency of the elongate flexible element 310 to roll or twist during a dissection procedure, while also providing additional retraction force to the target tissue. In addition, or alternatively, if the guide members are placed on the top of the parallel wires, stabilizer(s) 325 could be attached to the bottom surface of the parallel wires.

Figure 4A:
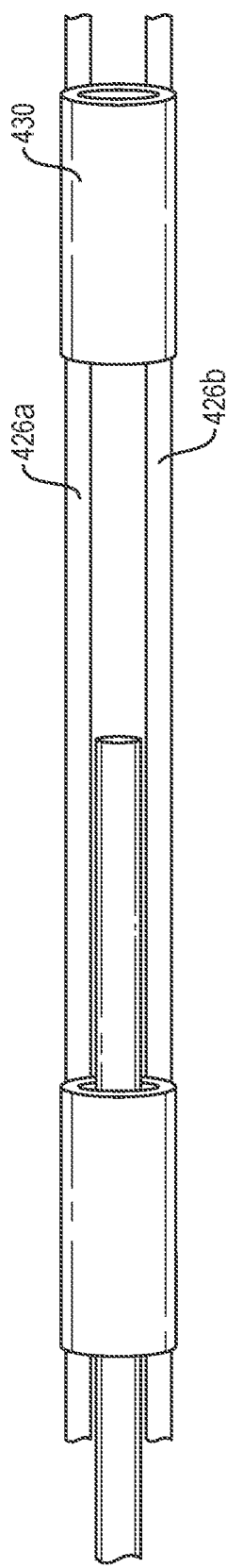
FIGS. 4A-4B illustrate a portion of a tissue retractor in a parallel (FIG. 4A) and bowed (FIG. 4B) configuration, according to an embodiment of the present disclosure.
Figure 4B:
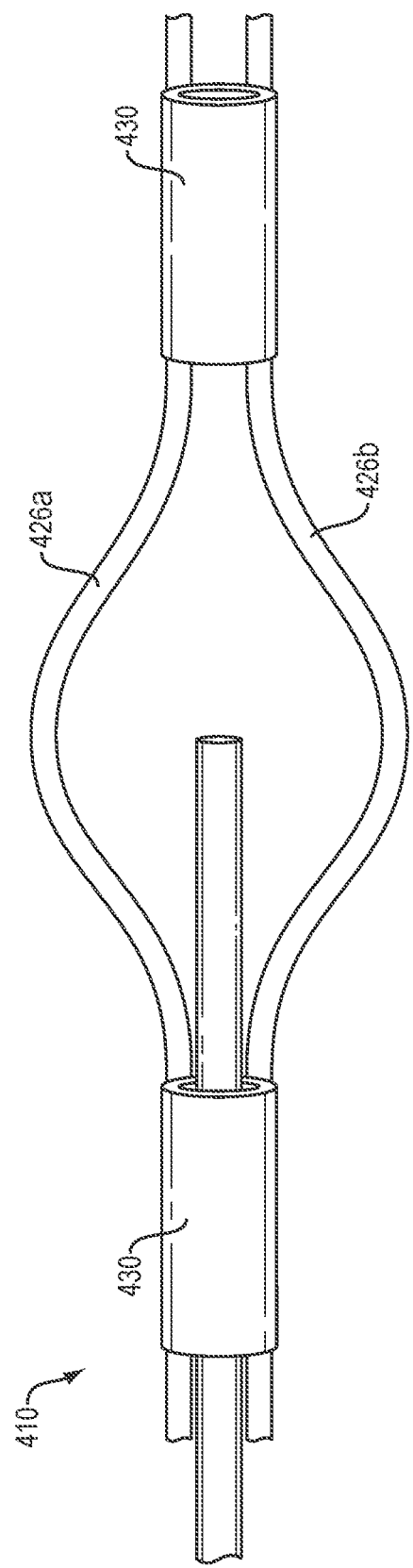

Referring to FIGS. 4A-4B, in one embodiment, a portion of the parallel wires 426a, 426b between one or more guide members 430 may splay or bow outward after deployment of the elongate flexible element 410 to provide one or more regions of increased surface area to provide additional stability (e.g., resistance to rolling or twisting). For example, one or more portions of the parallel wires 426a, 426b may be heat set during production such that the positions are straight when constrained (FIG. 4A) and bow outward upon exiting the delivery tube (FIG. 4B).

Figure 5:
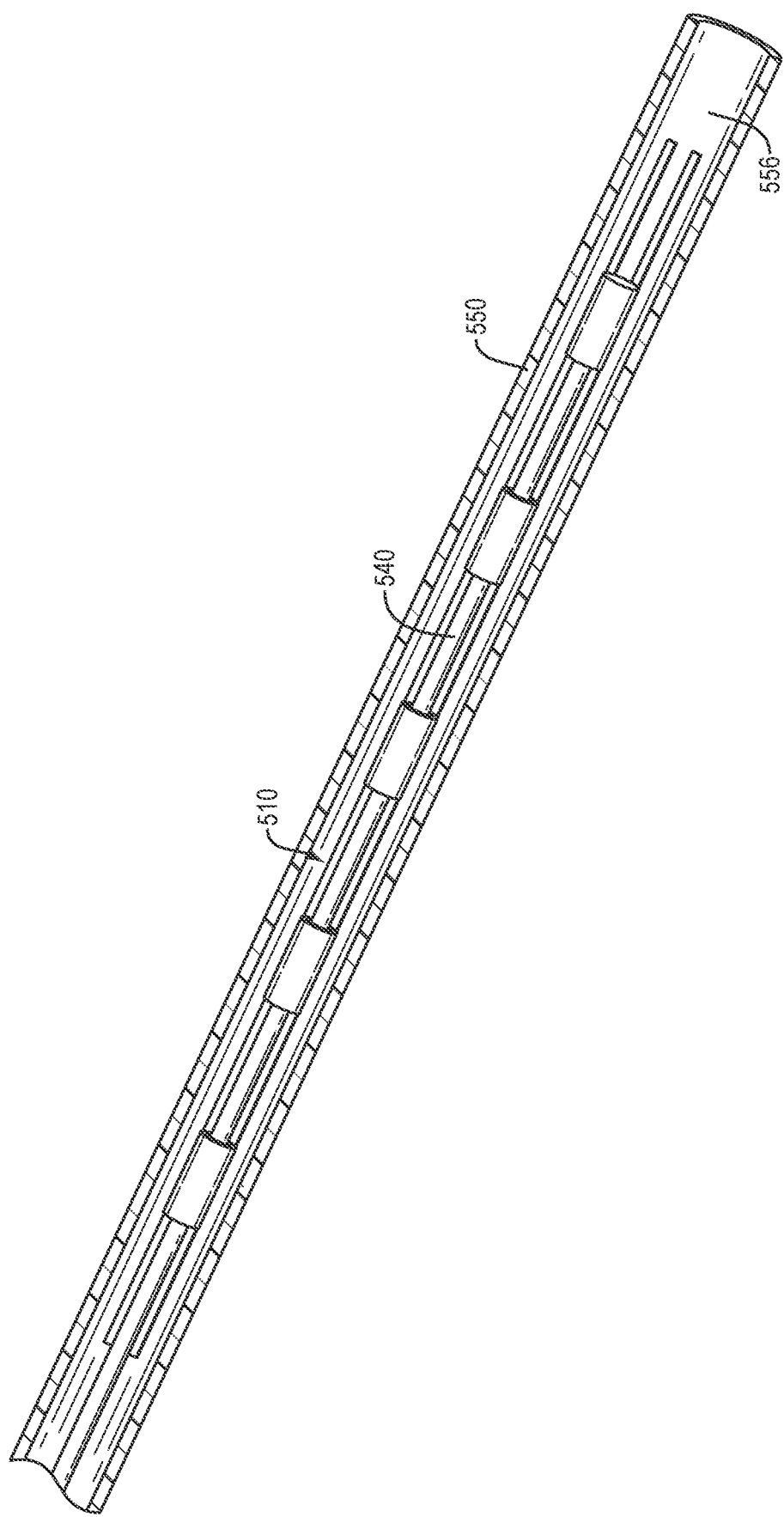
FIG. 5 illustrates the tissue retractor of FIG. 1A disposed within the lumen of a delivery system, according to an embodiment of the present disclosure.

Referring to FIG. 5, in one embodiment, the present disclosure may include a delivery system comprising an elongate flexible element 510 slidably disposed in a first (i.e., constrained) configuration within the lumen 556 of a delivery catheter 550 (e.g., over-tube, restraining sheath etc.). The control wire 540 may extend through the lumen 556 of the delivery catheter 550 such that a proximal end (not depicted) of the control wire 540 extends beyond a proximal end (not depicted) of the delivery catheter 550.

Referring to FIG. 6A, in use and by way of example, an endoscope 660 may be advanced into a body passage such that a distal end 664 of the endoscope 660 is positioned adjacent to a target tissue 72. A delivery system, such as the catheter of FIG. 5, may then be advanced through a working channel 666 of the endoscope 660 such that a distal end 654 of the delivery catheter 650 is positioned above a first portion of the target tissue 72. The proximal end of the control wire may then be advanced distally such that the distal end 614 of the elongate flexible element 610 moves beyond the distal end 654 of the delivery catheter 650. It should be appreciated that the cap 634 (FIG. 6B) of the distal-most guide member 630 provides a surface against which the control wire 640 may exert such distal force. The control wire 640 may be further distally advanced to embed the distal end 614 of the elongate flexible element 610 within a first portion of the target tissue 72. Alternatively, the control wire may be held in place and the catheter or endoscope advanced to embed the anchor. In one embodiment, the distal end 614 may move from a constrained to a deployed configuration as it exits the delivery catheter 650. The deployed configuration may provide a larger (i.e., broader) surface area for increased engagement with the target tissue. Referring to FIG. 6B, while applying (e.g., maintaining) distal force to the elongate flexible element 610 by the control wire 640, the delivery catheter 650 may be proximally retracted such that the proximal end 612 of the elongate flexible element 610 moves beyond the distal end 654 of the delivery catheter 650. Referring to FIG. 6C, the distal end 654 of the delivery catheter 650 may then be advanced distally such that a distal force is exerted or applied against the proximal end 612 of the elongate flexible element 610 to embed the proximal end 612 within a second portion of the target tissue 72. It should be appreciated the distal force exerted by the distal end 654 of the delivery catheter 650 against the proximal end 612 may cause the elongate flexible element 610 to bow or flex inward prior to (or during) embedding of the proximal end 612 within the second portion of the target tissue 72. As the distal force exerted by the distal end 654 of the delivery catheter 650 is removed, the elongate flexible element 610 may return to the un-flexed configuration to further press and engage the proximal and distal ends 612, 614 into respective first and second portions of the target tissue 72. Alternatively, enough distal pressure may be applied to the control wire itself to bow the elongate flexible element enough to embed the anchors without engaging the elongate flexible element with the distal end of delivery catheter. In addition, or alternatively still, the anchors themselves may be configured in a way so as to be self-seating or embedding with little or no distal pressure. Referring to FIG. 6D, the control wire 640 may then be proximally retracted and removed from within the respective lumens 632 of each guide member 630. With the control wire 640 removed, the elongate flexible element 610 may be further secured to the target tissue 72 due to the natural tendency of the elongate flexible element 610 to move from the first to second configuration, thereby applying upward and outward forces to proximal and distal ends 612, 614. Simultaneous pressure driving or pressing the second surface 618 of the elongate flexible element 610 against the surface of the target tissue 72 may also occur. It should also be appreciated that in certain surgical procedures it may be preferable to embed one or both of the proximal and distal ends 612, 614 within a healthy (e.g., non-diseased) portion of the tissue outside or beyond the margin of the target tissue to minimize the possibility of dislodging cancerous cells that might promote metastasis. In such a case, tissue may be retracted from only the side of the elongate flexible element that has an anchor embedded within tissue to be dissected.

Figure 7A:
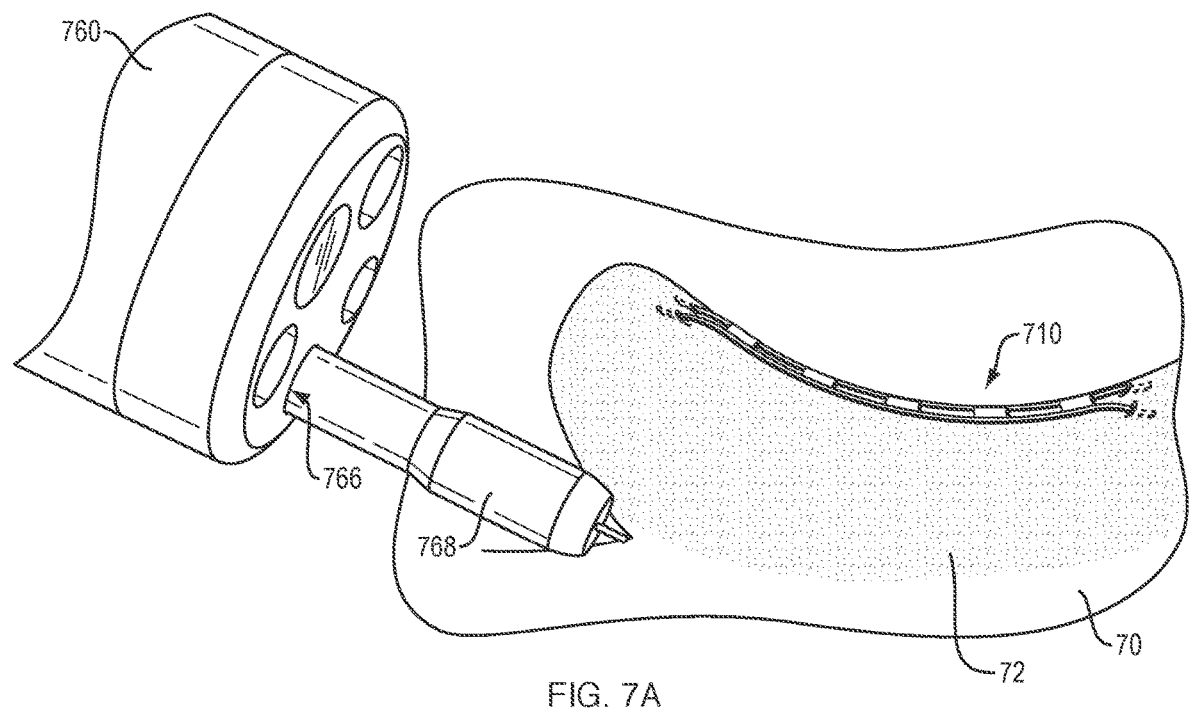
FIGS. 7A-7C illustrate a dissection of a target tissue using a tissue retractor, according to an embodiment of the present disclosure.
Figure 7B:
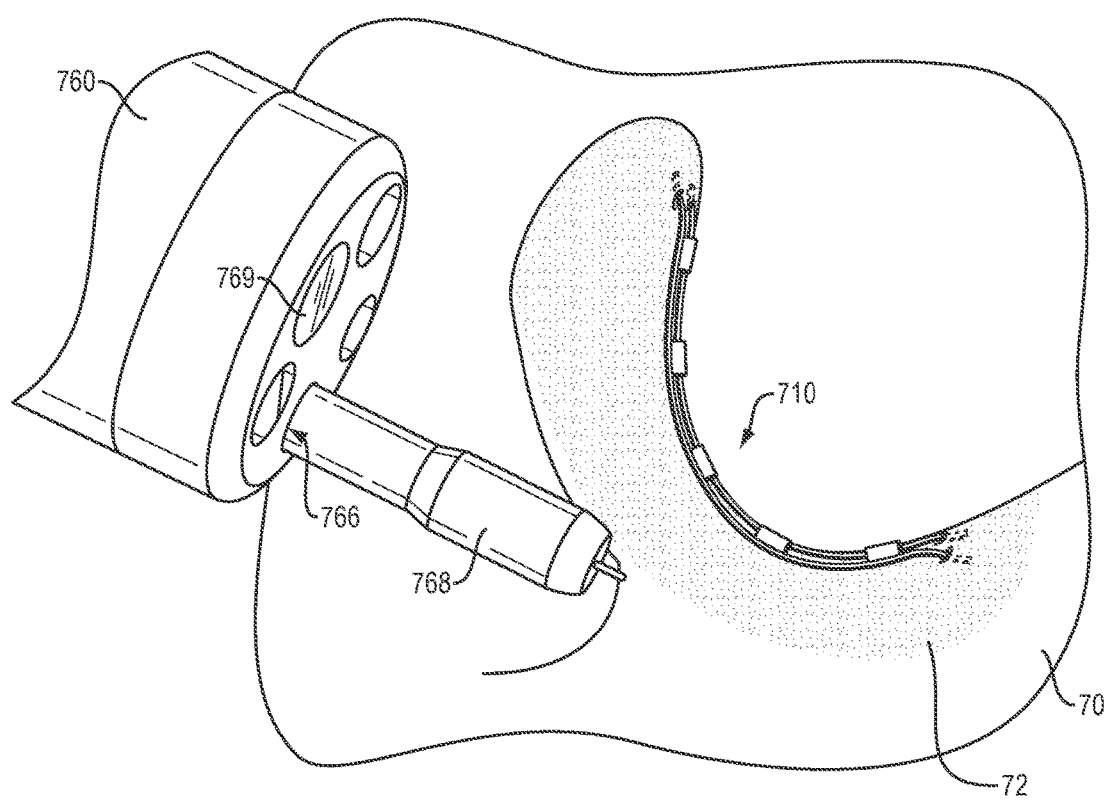
Figure 7C:
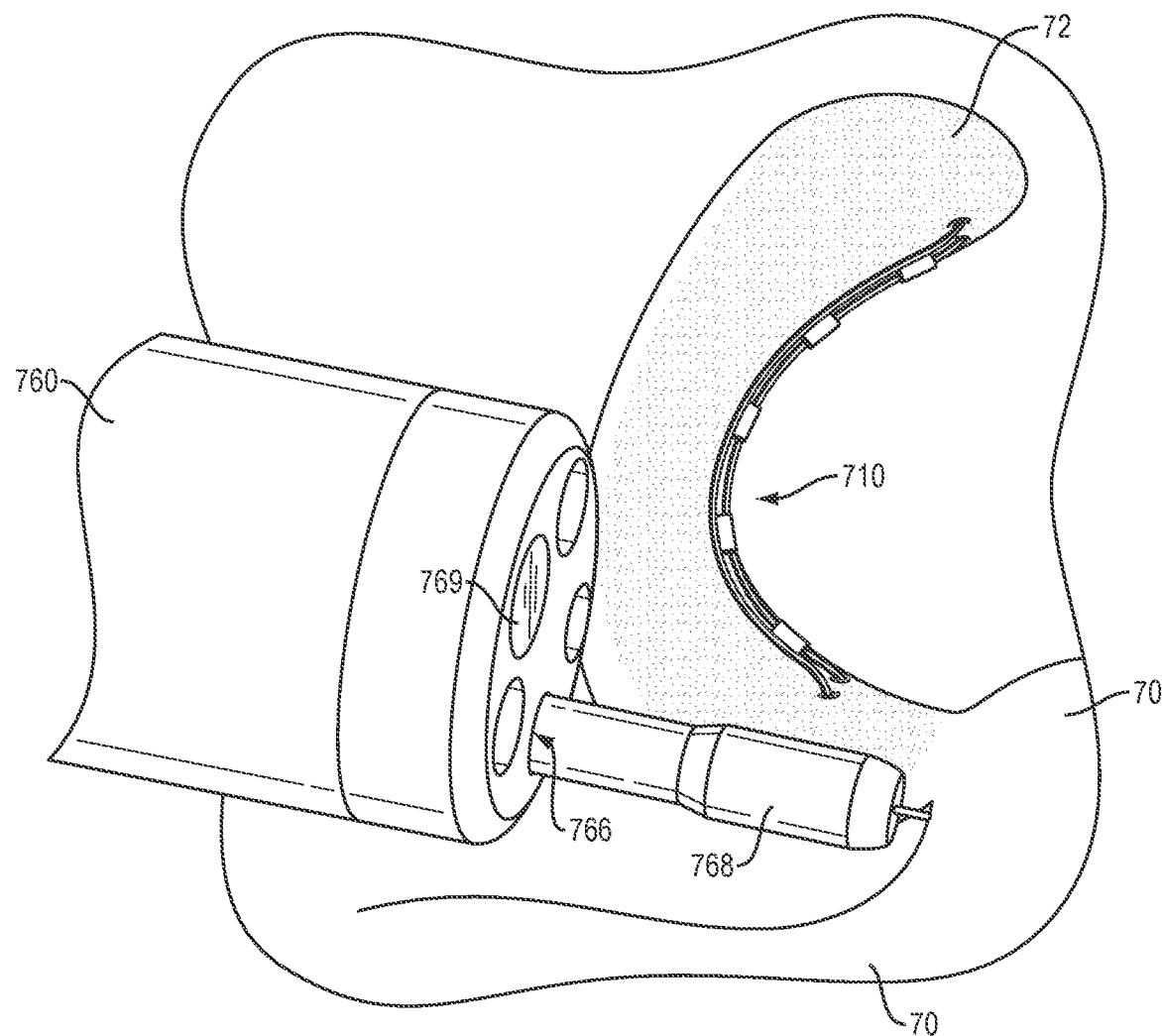

Referring to FIGS. 7A-7C, a cutting element 768 may then be advanced through a working channel 766 of the endoscope 760 to dissect the target tissue 72 from the surrounding healthy tissue 70. As the target tissue 72 is dissected, the portion of the elongate flexible element 710 attached to the dissected tissue moves from the first to second configuration, lifting and pulling the dissected target tissue 72 away from the cutting element 768 and endoscope camera 769. Once the target tissue is fully dissected, the elongate flexible element 710 and attached target tissue 72 may be removed for biopsy through a working channel 766 of the endoscope 760 using a suitable grasping element (not depicted). Alternatively, the elongate flexible element 710 and attached target tissue 72 may be allowed to remain within the body passage for removal by the body's natural course. Importantly, the elongate flexible element 710 does not occupy a working channel 766 of the endoscope 760 during the dissection procedure, thereby allowing the medical professional to introduce and manipulate additional medical tools as required for a given medical procedure.

Referring to FIGS. 8A-8B, in one embodiment, a tissue retractor of the present disclosure may include an elongate flexible element 810 comprising a mesh-like structure that may be formed from a variety of woven or interlaced shape polymers, metals or alloys. The proximal and distal ends 812, 814, of the elongate flexible element 810 may include a plurality of free wire ends 824 (e.g., wire sharps) configured to engage first and second target tissue portions in a "Velcro-like" manner. In one embodiment, a surface of the elongate flexible element 810 may include one or more guide members configured to receive a control wire (not depicted). As above, the control wire may maintain the elongate flexible element 810 in a first (i.e., constrained) configuration when disposed within the central lumen (FIG. 8A), and allow the elongate flexible element to return to the second (i.e., relaxed) configuration when not disposed within the central lumen (FIG. 8B). The elongate flexible element 810 may be deployed into and onto a target tissue using a delivery catheter and endoscope, as discussed above.

Figure 9:
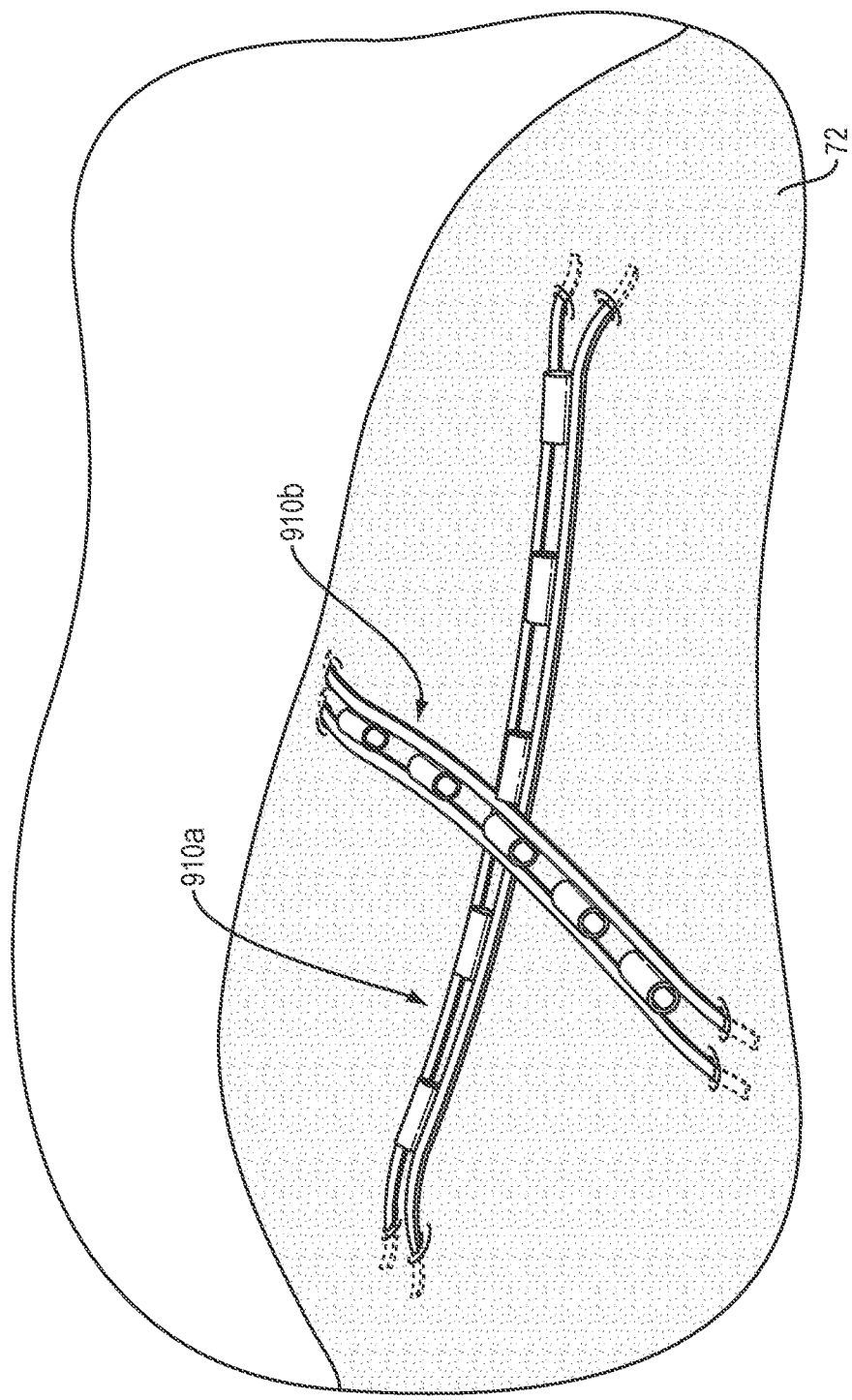
FIG. 9 illustrates two tissue retractors deployed along opposing planes of a target tissue, according to an embodiment of the present disclosure.

Referring to FIG. 9, in one embodiment, one or more elongate flexible elements 910a, 910b may be deployed onto a target tissue 72 to provide multiple planes of tissue retraction. For example, a first elongate flexible element 910a may deployed along a first plane of the target tissue 72 and a second elongate flexible element 910b may deployed over and perpendicular to the first elongate flexible element 910a along a second plane of the target tissue 72. It should be appreciated that the multiple planes of retraction afforded by the use of multiple elongate flexible elements may provide the tissue retraction forces required to safely and efficiently dissect large and/or irregularly shaped target tissues, or to dissect tissues in and around delicate anatomical structures.

Referring to FIG. 10A, in one embodiment, a tissue retractor of the present disclosure may include an elongate flexible element 1010, as discussed above, and further comprise first and second arms 1028a, 1028b (e.g., strips, petals, legs etc.) extending radially outward from a central portion 1013 of the elongate flexible element 1010. An end 1029a of the first arm 1028a may be configured to engage a third target tissue portion, and an end 1029b of the second arm 1028b may be configured to engage a fourth target tissue portion. A plurality of guide members 1030 may be disposed along the first surface 1016 (e.g., top surface) of the first and second arms 1028a, 1028b. Each guide member 1030 may define a lumen 1032 extending therethrough. In one embodiment, an end of the distal-most guide member 1030 on each of the first and second arms 1028a, 1028b (i.e., the guide member closest to the ends 1029a, 1029b) may include a cap 1034 to provide a surface against which control wires may exert distal force. To this end, the tissue retractor may further include first and second control wires 1040a, 1040b configured to be slidably received by the respective lumens 1032 of each guide member 1030 disposed along the first surface 1016 of the first and second arms 1028a, 1028b. For example, the first control wire 1040a may extend along the first surface 1016 of the proximal portion 1017 of the elongate flexible element 1010, and turn approximately 90 degrees at the central portion 1013 to be slidably received by the lumens 1032 of guide members 1030 on the first arm 1028a. A second control wire 1040b may extend parallel to the first control wire 1040a along the first surface 106 of the proximal portion 1017 of the elongate flexible element 1010, and turn approximately 90 degrees at the central portion 1013 to be slidably received by the lumens 1032 of guide members 1030 on the second arm 1028b. Although not illustrated, an additional control wire (i.e., third control wire) may disposed along a second surface 1018 (e.g., bottom surface) of the elongate flexible element 1010, e.g., as outlined in FIGS. 1A-1B. When the first and second control wires 1040a, 1040b are disposed within the respective lumens 1032 of each guide member 1030, the first and second arms 1028a, 1028b are maintained in a first (i.e., constrained) configuration. Referring to FIG. 10B, when the first and second control wires 1040a, 1040b are not disposed within (i.e., removed from) the respective lumens 1032 of each guide member 1030, the first and second arms 1028a, 1028b move to a second (i.e., relaxed) configuration. It should be appreciated that the "force" stored within such materials when in the constrained configuration may be such as to allow the elongate flexible element 1010 to apply and maintain constant upward lifting/retraction pressure along multiple planes of the target tissue in which it is embedded.

The tissue retractor illustrated in FIG. 10B may be slidably disposed within the lumen of a delivery catheter as discussed above. In one embodiment, the elongate flexible element 1010 portion of the tissue retractor may be deployed onto a target tissue site by following the steps outlined above. The first and second control wires 1040a, 1040b may then be advanced distally to urge the first and second arms 1028a, 1028b outward into a planar configuration (FIG. 10A) such that the ends 1029a, 1029b engage respective third and fourth tissue portions. It should be appreciated that the arms of the elongate flexible element may be fashioned in any variety of shape and the ends 1029a, 1029b of each arm may include any manner of tissue anchor configurations, including as illustrated in FIGS. 2A-2D.

Figure 11A:
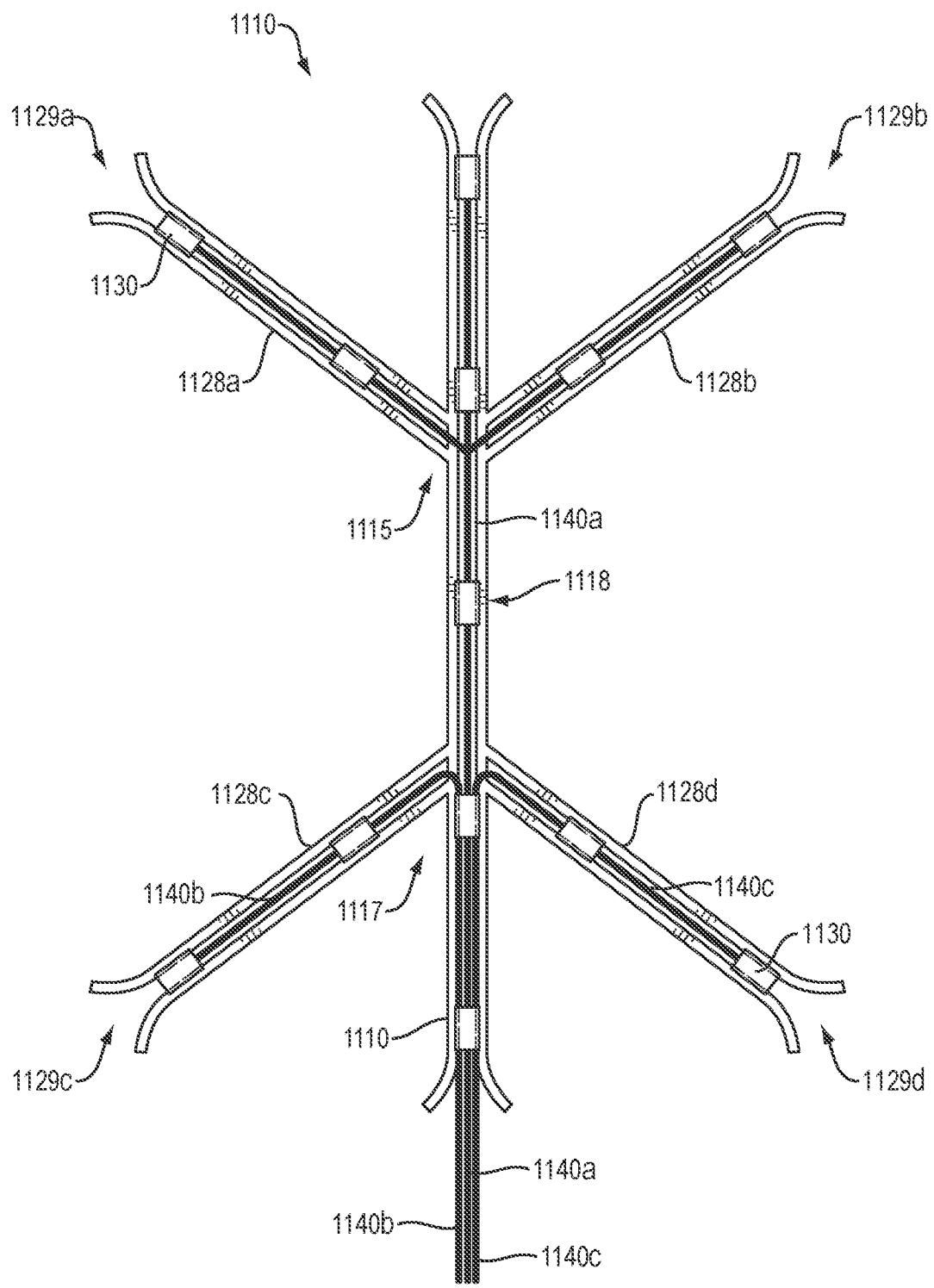
FIGS. 11A-11C illustrate a tissue retractor in constrained (FIG. 11A), relaxed (FIG. 11B) and delivery (FIG. 11C) configurations, according to another embodiment of the present disclosure.

Referring to FIG. 11A, in another embodiment, a tissue retractor of the present disclosure may include an elongate flexible element 1110, as illustrated in FIG. 1A, which further comprises first and second arms 1128a, 1128b extending radially from a distal portion 1115 of the elongate flexible element 1110, and third and fourth arms 1128c, 1128d extending radially from a proximal portion 1117 of the elongate flexible element 1110. An end 1129a of the first arm 1128a may be configured to engage a third target tissue portion, an end 1129b of the second arm 1128b may be configured to engage a fourth target tissue portion, an end 1129c of the third arm 1128c may be configured to engage a fifth target tissue portion and an end 1129d of the fourth arm 1128d may be configured to engage a sixth target tissue portion. A plurality of guide members 1130 may be disposed along the first surface 1118 (i.e., top surface) of the first, second, third and fourth arms 1128a-d. Each guide member 1130 may define a lumen extending therethrough. In one embodiment, the distal-most guide member 1130 on each of the first, second, third and fourth arms 1128a-d (i.e., the guide member closest to the ends 1129a-d) may include an end cap to provide a surface against which a control wire may exert distal force. To this end, the tissue retractor may further include first, second and third control wires 1140a, 1140b, 1140c configured to be slidably received by the respective lumens of each guide member 1130 disposed along the first surface 1118 of the first, second, third and fourth arms 1128a-d. For example, the first control wire 1140a may extend along the first surface 1118 the elongate flexible element 1110, and include a forked or split end configured to be slidably received by the lumens of guide members 1130 on the first and second arms 1128a, 1128b. Alternatively, the elongate flexible element 1110, first arm 1128a and second arm 1128b may include separate/distinct control wires (not depicted) to allow independent deployment. The second control wire 1140b may extend parallel to a portion of the first control wire 1140a, and turn beyond 90 degrees at proximal portion 1117 of the elongate flexible element 1110 to be slidably received by the lumens of guide members 1130 on the third arm 1128c. The third control wire 1140c may extend parallel to a portion of the first control wire 1140a, and turn beyond 90 degrees at proximal portion 1117 of the elongate flexible element 1110 to be slidably received by the lumens of guide members 1130 on the fourth arm 1128d. Although not illustrated, an additional control wire (i.e., fourth control wire) may disposed along a second surface (i.e., bottom surface) of the elongate flexible element 1110, e.g., as outlined in FIGS. 1A-1B.

Figure 11B:
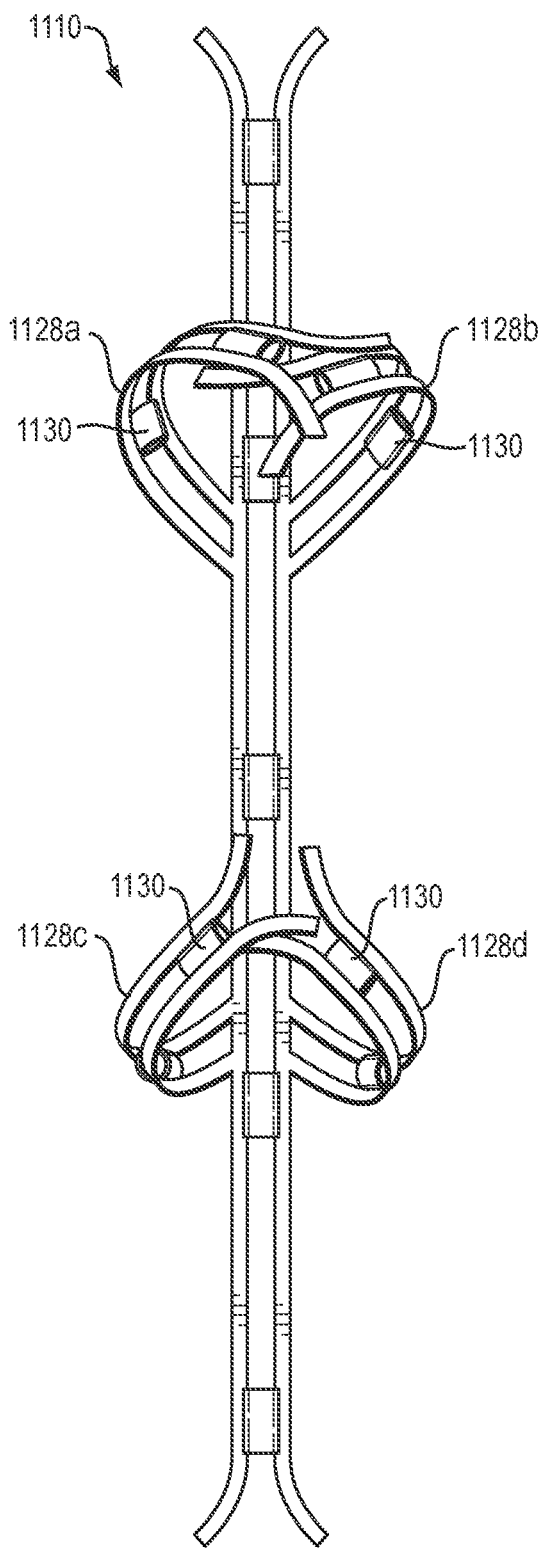
Figure 11C:
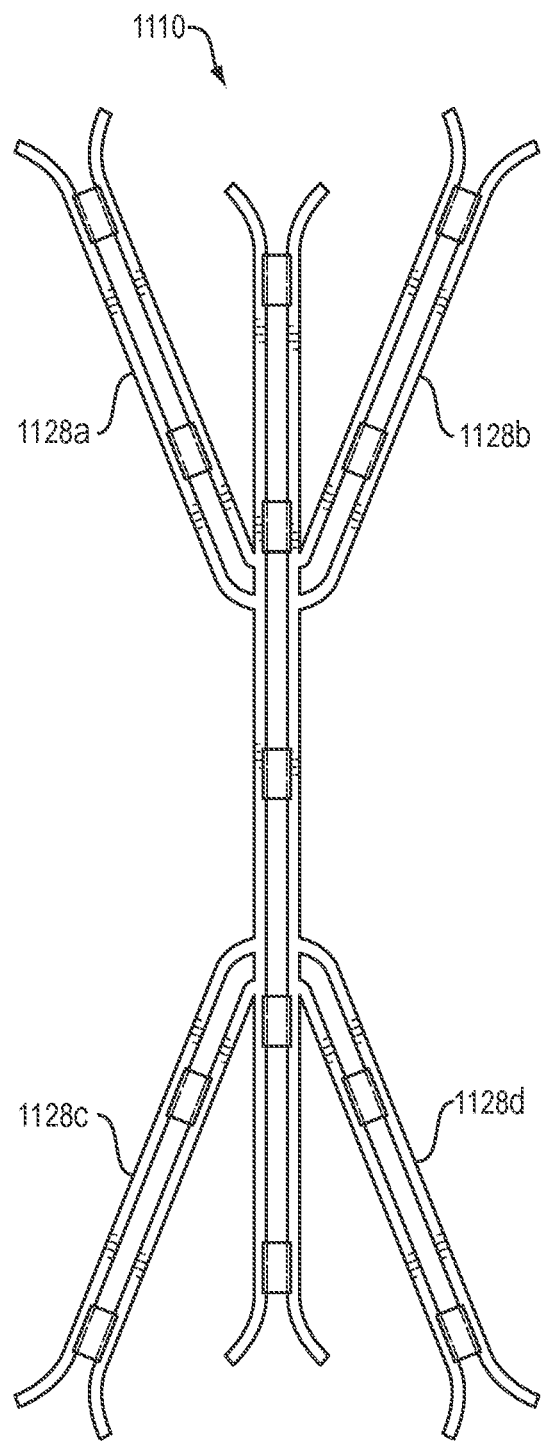

When the first, second and third control wires 1140a-c are disposed within the respective lumens of each guide member 1130, the first, second, third and fourth arms 1128a-d are maintained in a first (i.e., constrained) configuration. Referring to FIG. 11B, when the first, second and third control wires 1140a-c (not depicted) are not disposed within (i.e., removed from) the respective lumens of each guide member 1130, the first, second, third and fourth arms 1128a-d move to a second (i.e., relaxed) configuration. In addition, or alternatively, the distal and proximal arms along the longitudinal axis may fold up into a second configuration when unconstrained similar to the other arms. Referring to FIG. 11C, in one embodiment the first, second, third and fourth arms 1128a-d may be formed from a sufficiently flexible or deformable material that they are able to collapse inward along the elongate flexible element 1110 when constrained within the lumen of a delivery catheter. It should be appreciated that the "force" stored within such materials when in the constrained configuration may be such as to allow the elongate flexible element 1110 to apply and maintain constant upward lifting/retraction pressure along multiple planes of the target tissue in which it is embedded.

The tissue retractor illustrated in FIG. 11C may be slidably disposed within the lumen of a delivery catheter as discussed above. In one embodiment, the elongate flexible element 1110 portion of the tissue retractor may be deployed onto a target tissue site by following the steps outlined above. The first, second and third control wires (not depicted) may then be advanced distally to urge the first, second, third and fourth arms 1128*a-d* outward into an expanded configuration (FIG. 11A) such that the ends 1129*a-d* engage respective third, fourth, fifth and sixth tissue portions. It should be appreciated that the ends 1129*a-d* of each arm may include any manner of tissue anchor configurations, including as illustrated in FIGS. 2A-2D.

Figure 12B:
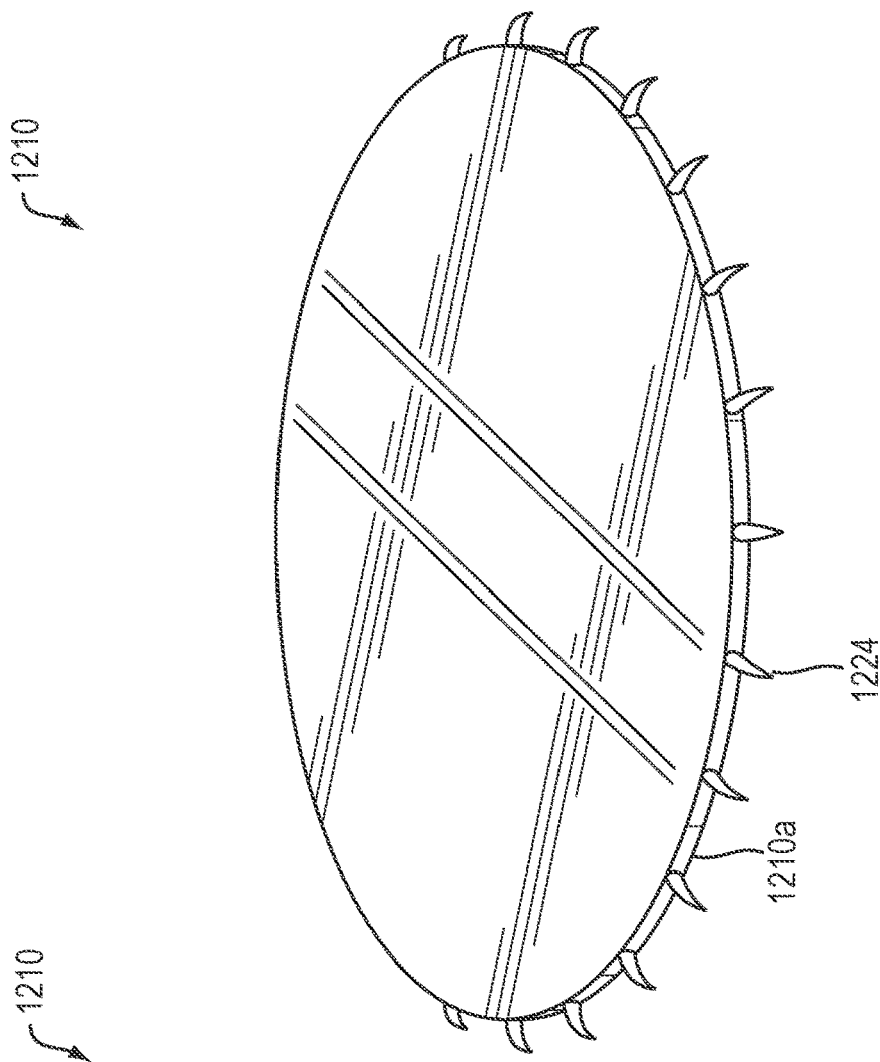
FIGS. 12A-12B illustrate a tissue retractor in constrained (FIG. 12A) and relaxed (FIG. 12B) configurations, according to another embodiment of the present disclosure.
Figure 12A:
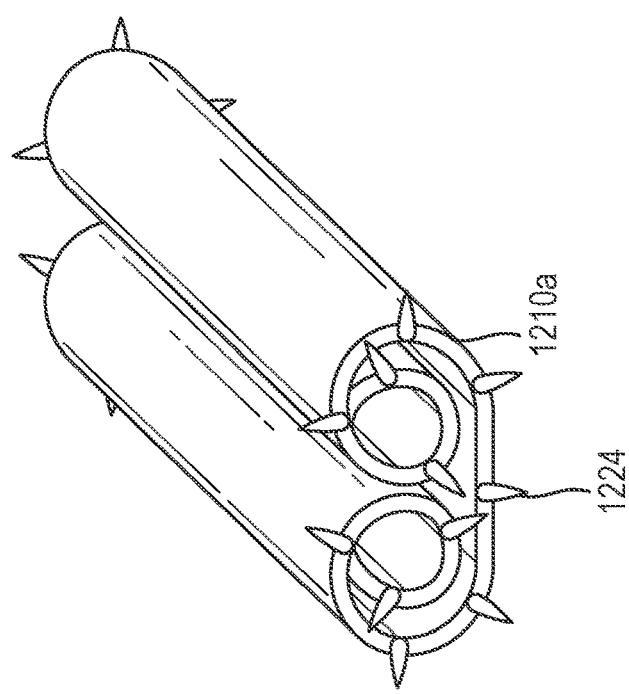

Referring to FIGS. 12A-12B, in one embodiment, a tissue retractor of the present disclosure may include a sheet 1210 of shape memory material configured to move between a first (i.e., constrained) configuration (FIG. 12B) and a second (i.e., relaxed, rolled or collapsed) configuration (FIG. 12A). A plurality of tissue anchors 1224 may be disposed about a perimeter 1210*a* of the sheet 1210. Although the tissue anchors 1224 of FIGS. 12A-12B are substantially evenly spaced along the perimeter 1210*a* of the sheet 1210, it should be appreciated that the tissue anchors may be disposed about the perimeter 1210*a* in a uniform or non-uniform pattern. It should be appreciated that the "force" stored within such shape memory materials may be such as to allow the sheet 1210 to apply and maintain constant upward lifting/retraction pressure along multiple planes of the target tissue in which it is embedded. As illustrated in FIG. 12A, the sheet 1210 may be delivered rolled into a first relaxed, cylindrical configuration and slidably disposed and constrained within the lumen of a delivery catheter (not depicted), like the elongate flexible element of FIGS. 1A-1B. The sheet 1210 may be advanced distally beyond the distal end of the delivery catheter and unrolled to assume a second constrained configuration of FIG. 12B, thereby allowing the tissue anchors 1224 to engage multiple portions of the target tissue. In addition, or alternatively, a medical device (i.e., biopsy forceps etc.) may be advanced through the delivery catheter to precisely position the sheet 1210 and apply sufficient pressure to engage at least some of the tissue anchors 1224 within the target tissue. Once the sheet 1210 is secured to the target tissue in the second configuration (FIG. 12B), a center portion of the sheet 1210 may be contacted (i.e., struck, tapped, hit etc.) with the medical device to stimulate the sheet 1210 to attempt to return to the first shape memory configuration (FIG. 12A), thereby exerting upward lifting/retracting pressure to the target tissue, as discussed above. It should be appreciated that the tissue retractors described herein may include any number, shape, dimension and/or orientation of arms and tissue anchors.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:
1. A tissue retractor, comprising:
a flexible element comprising:
a sheet having a perimeter; and
a plurality of anchors disposed about the sheet configured to engage tissue;
wherein the flexible element is movable between a relaxed configuration wherein the sheet is rolled, and a constrained configuration wherein the sheet is substantially planar.

2. A tissue retractor comprising:
a flexible element comprising:
a sheet having a perimeter; and
a plurality of anchors disposed about the sheet configured to engage tissue; wherein:
the flexible element is movable between a first configuration wherein the sheet is rolled and a second configuration wherein the sheet is substantially planar; and
the first configuration and the second configuration are each heat set stable states of the flexible element.

3. The tissue retractor of claim 2, wherein the flexible element is configured to move from the second configuration to the first configuration in response to an application of force on the sheet.

4. The tissue retractor of claim 1, wherein the sheet of the flexible element forms at least one cylindrical shape when rolled in the relaxed configuration.

5. A tissue retractor comprising:
a flexible element comprising:
a sheet having a perimeter; and
a plurality of anchors disposed about the sheet configured to engage tissue; wherein:
the flexible element is movable between a first configuration wherein the sheet is rolled, and a second configuration wherein the sheet is substantially planar; and
the flexible element is pre-formed to the first configuration such that the flexible element is in the first configuration when unconstrained.

6. The tissue retractor of claim 1, wherein the plurality of anchors are tines, forks, hooks, fingers, barbs, or clips, or combinations thereof.

7. The tissue retractor of claim 5, wherein the plurality of anchors are arranged in a symmetrical array about the perimeter of the sheet.

8. The tissue retractor of claim 1, wherein the relaxed configuration and the constrained configuration are each heat set stable states of the flexible element.

9. The tissue retractor of claim 1, wherein the flexible element is configured to move from the constrained configuration to the relaxed configuration in response to an application of force on the sheet.

10. The tissue retractor of claim 1, wherein the flexible element is pre-formed to the relaxed configuration such that the flexible element is in the relaxed configuration when unconstrained.

11. The tissue retractor of claim 1, wherein the plurality of anchors are along a periphery of the sheet.

12. The tissue retractor of claim 1, wherein the sheet curls along a longitudinal axis thereof.

13. The tissue retractor of claim 2, wherein the first configuration is a relaxed configuration, and the second configuration is a constrained configuration.

14. The tissue retractor of claim 2, wherein the sheet of the flexible element forms at least one generally cylindrical shape when rolled in the first configuration.

15. The tissue retractor of claim 2, wherein the flexible element is pre-formed to the first configuration such that the flexible element is in the first configuration when unconstrained.

16. The tissue retractor of claim 2, wherein the plurality of anchors are tines, forks, hooks, fingers, barbs, or clips, or combinations thereof.

17. The tissue retractor of claim 2, wherein the plurality of anchors are along a periphery of the sheet.

18. The tissue retractor of claim 5, wherein the flexible element is configured to move from the second configuration to the first configuration in response to an application of force on the sheet.

19. The tissue retractor of claim 5, wherein the plurality of anchors are tines, forks, hooks, fingers, barbs, or clips, or combinations thereof.

20. The tissue retractor of claim 5, wherein the plurality of anchors are along a periphery of the sheet.

\* \* \* \* \*